US00PP26874P3

(12) United States Plant Patent
Vinson et al.

(10) Patent No.: US PP26,874 P3
(45) Date of Patent: Jun. 28, 2016

(54) STRAWBERRY PLANT NAMED 'SSL 93'

(50) Latin Name: *Fragaria×ananassa*
Varietal Denomination: SSL 93

(71) Applicants: Peter Edward Vinson, Kent (GB); Ilona Eva McCarthy, Kent (GB)

(72) Inventors: Peter Edward Vinson, Kent (GB); Ilona Eva McCarthy, Kent (GB)

(73) Assignee: Edward Vinson Limited, Kent (GB)

( * ) Notice: Subject to any disclaimer, the term of this patent is extended or adjusted under 35 U.S.C. 154(b) by 143 days.

(21) Appl. No.: 13/999,610

(22) Filed: Mar. 12, 2014

(65) Prior Publication Data

US 2014/0298549 P1 Oct. 2, 2014

(30) Foreign Application Priority Data

Mar. 27, 2013 (EM) ..... 2013/0940

(51) Int. Cl.
*A01H 5/08* (2006.01)

(52) U.S. Cl.
USPC ..... Plt./208
CPC ..... *A01H 5/0893* (2013.01)

(58) Field of Classification Search
USPC ..... Plt./208
See application file for complete search history.

*Primary Examiner* — Keith Robinson
(74) *Attorney, Agent, or Firm* — Penny J. Aguirre

(57) ABSTRACT

A new and distinct short day Mediterranean cultivar of strawberry plant named 'SSL 93' that is characterized by its upright, semi-compact and dense growth habit, its conical to cordate shaped berries that are uniformly large to medium in size, its berries with very firm skin and moderately juicy, soft flesh, its berries that are highly glossy and bright medium orange-red in color, its moderately vigorous growth with substantial fruit yield, its short day fruiting habit with early season production, its excellent tolerance to fruit skin damage caused by bruising, its moderate to heavy petiole pubescence, and its tolerance to *Botryotinia cinerea* and slight susceptibility to *Podosphaera leucotricha* (powdery mildew) and *Phytophtora cactorum* (crown rot).

2 Drawing Sheets

Botanical classification: *Fragaria×ananassa.*
Variety denomination: 'SSL 93'.

BACKGROUND OF THE INVENTION

The present invention relates to a new and distinct cultivar of *Fragaria*, botanically known as *Fragaria×ananassa* 'SSL 93', and will be referred to hereafter by its cultivar name, 'SSL 93'. 'SSL 93' is a Mediterranean short day strawberry primarily adapted to the climate and growing conditions of the Mediterranean and other regions of similar climate and day length.

The new cultivar was derived from an ongoing breeding program conducted by the Inventors at a farm in Cartaya, Huelva, Spain. 'SSL 93' arose from a controlled cross made by the Inventors in 2008 between an unnamed selection from the Inventors breeding program, designated as accession number 'SVE72' as the female parent and an unnamed selection from the Inventors breeding program, designated as accession number 'S06WL48' as the male parent. 'SSL 93' was selected as a single unique plant in summer of 2009 from amongst the seedlings that resulted from the above cross.

Asexual propagation of the new cultivar was first accomplished by rooting of stolons by the Inventor in Kent, United Kingdom in 2010. Asexual propagation by rooting of stolons has shown that the unique characteristics of the new cultivar are stable and reproduced true to type in successive generations.

BRIEF SUMMARY OF THE INVENTION

The following traits have been repeatedly observed and are determined to be characteristics of the new cultivar of strawberry. These attributes in combination distinguish 'SSL 93' as unique from all other strawberry cultivars known to the Inventor. 'SSL 93' is well adapted for the growing conditions in Spain.

1. 'SSL 93' exhibits an upright semi-compact growth habit.
2. 'SSL 93' exhibits conical shaped berries that are uniformly medium large in size.
3. 'SSL 93' exhibits berries with firm skin and juicy, soft flesh.
4. 'SSL 93' produces berries that contain high sugars and have exceptional flavor.
5. 'SSL 93' exhibits berries that are glossy and bright orange-red in color with color retained throughout production.
6. 'SSL 93' exhibits vigorous growth with substantial fruit yields.
7. 'SSL 93' exhibits heavy petiole pubescence.
8. 'SSL 93' exhibits tolerance to *Botryotinia cinerea* and slight susceptibility to *Podosphaera leucotricha* (powdery mildew) and *Phytophtora cactorum* (crown rot).

'SVE72', the female parent of 'SSL 93', differs from 'SSL 93' in having berries that are conical in shape, higher in acidity, and darker red in color. 'S06WL48', the male parent of 'SSL 93', differs from 'SSL 93', in producing a moderate yield of berries with outstanding flavor, soft skin and complex trusses.

'SSL 93' can be most closely compared to the cultivar 'Viva Patricia' (U.S. Plant Pat. No. 22,717) with the following comparison characteristics observed under growing conditions in Spain. 'SSL 93' produces slightly smaller fruit than 'Viva Patricia' and has a fruit shape that is less elongated than that of 'Viva Patricia', however 'SSL 93' is more even in shape. The fruit skin of 'SSL 93' is firmer than that of 'Viva Patricia', a similar flower truss length to that of 'Viva Patricia', and a flat to slightly re-curved calyx position relative to the fruit. Furthermore, the fruit of 'SSL 93' has a better shelf life and is less prone to infections by botrytis (*Botryotinia cinerea*) than that of 'Viva Patricia'.

'SSL 93' plants exhibit a similarly vigorous growth habit to that of 'Viva Patricia', however when it is grown in Spain, the plant size of 'SSL 93' is slightly smaller than 'Viva Patricia'. The leaf size of 'SSL 93' is medium, but slightly larger than that of 'Viva Patricia'.

The petiole lengths of 'SSL 93' are slightly greater than that of 'Viva Patricia', however the petiolule lengths are smaller. Moderate to heavy pubescence is present on 'SSL 93' particularly at the base of the petiole and close to the stipules resulting in a significantly heavier pubescence than that of 'Viva Patricia'. The petiolule pubescence of 'SSL 93' is moderate, but still considerably more than that of 'Viva Patricia'.

The leaflets of 'SSL 93' typically possess a slightly round (obtuse) base and tip; however, the leaflets are not symmetrical. In fact, the leaflets of 'SSL 93' express a very distinctive architecture wherein the distance from the petiolule to the first serration is significantly longer on one side compared to the other (approximately 20%). The serrations express slightly pointed to slightly rounded tips with the leaflets of 'SSL 93', plants possessing a similar number of serrations per leaf to that of 'Viva Patricia'. The most outstanding difference between the two varieties is expressed in the plant architecture, where the plants of 'SSL 93' are very upright and semi-compact with mostly concave leaves, whereas the plants of 'Viva Patricia' express a more spreading habit with the majority of leaves being flat to slightly concave. Many leaflets of 'SSL 93' exhibit slight to moderate puckering/blistering, whereas the leaves of 'Viva Patricia' express very little or no puckering/blistering.

'SSL 93' flower trusses tend to grow within the foliage and do not stand out of the leaf canopy however, a small percentage, approximately 10%, of the overall trusses are exposed over the leaf canopy. All fruit trusses, when loaded with fruit, tend to protrude to the sides of the plant between the leaves rather than expressing a totally upward direction. The presence of a bract can be seen on 80% of the flower trusses from early developmental stage, which progresses into a typical single leaflet as the truss matures and fruit develops.

The primary flowers of 'SSL 93' are slightly smaller than those of 'Viva Patricia'. Petal numbers of 'SSL 93' are similar to that of 'Viva Patricia'. The calyx diameter of 'SSL 93' is significantly larger than that of 'Viva Patricia'. The calyxes of 'SSL 93' are typically flat touching the shoulders of the fruit, however some are re-curving expressing a very narrow fruit neck at the top of the berry.

The berries of 'SSL 93' are highly glossy, are medium to large in size with a shape that is predominantly conical to cordate with broad shoulders. When grown in Spain, the fruit of 'SSL 93' has an even uniform shape without any white band around the neck, a feature that is prominent in the fruit of 'Viva Patricia', particularly in the early part of the season.

'SSL 93' berries are slightly paler orange-red than those of 'Viva Patricia'. During the cropping season, the fruit of 'SSL 93' retains its bright orange-red color and appears to be unaffected by the higher seasonal temperatures.

The achenes of 'SSL 93' berries are characterized as being generally level with the surface of the fruit, compared to 'Viva Patricia' that features achenes that are generally even to slightly indented into the surface of the fruit. 'SSL 93' berries generally contain slightly more achenes than those of 'Viva Patricia'.

The berries of 'SSL 93' are noticeably firmer than those of 'Viva Patricia' throughout the cropping season with a pleasant combination of flavor, sugar and low acid levels. The berry skin of 'SSL 93' is firmer than that of 'Viva Patricia' and resists bruising better during rubbing than the latter. The fruit flesh of 'SSL 93' is slightly drier than that of 'Viva Patricia' resulting in an intense sweetness with soft texture and a very pleasant eating experience.

Professional taste panels in the UK have graded the flavor of 'SSL 93' greater than 'Viva Patricia' and a wide range of other varieties.

BRIEF DESCRIPTION OF THE DRAWINGS

The accompanying colored photographs illustrate the overall appearance and distinct characteristics of the new *Fragaria*. The photographs were taken of five month-old plants of 'SSL 93' as grown outdoors in field trials with tunnels and polyethylene covers in Cartaya, Huelva, Spain.

The photograph in FIG. 1 provides a view of the dense plant habit of 'SSL 93' and fruit in various stages of development.

Figure 1:
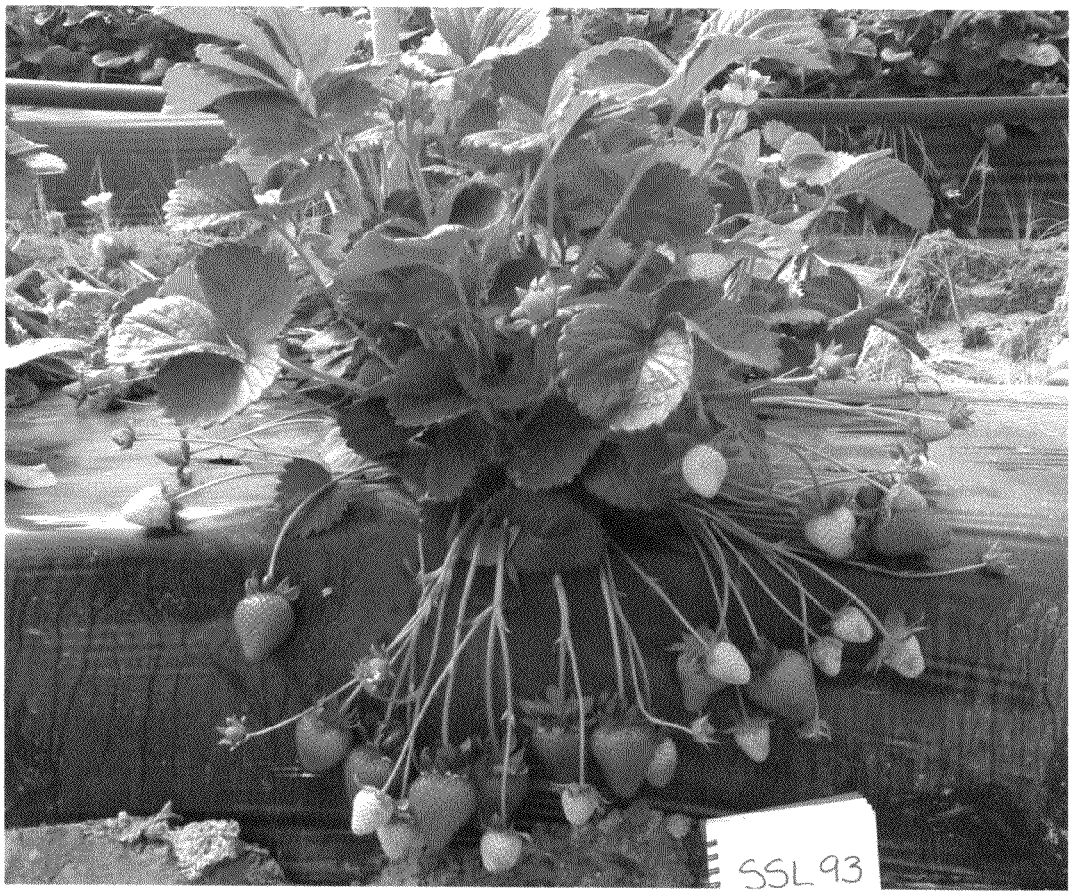
Figure 2:
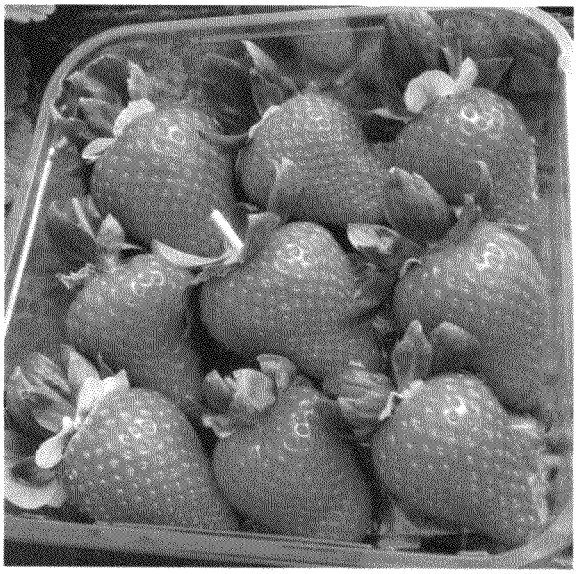

The photograph in FIG. 2 provides a close-up view of the berries of 'SSL 93'.

Figure 3:
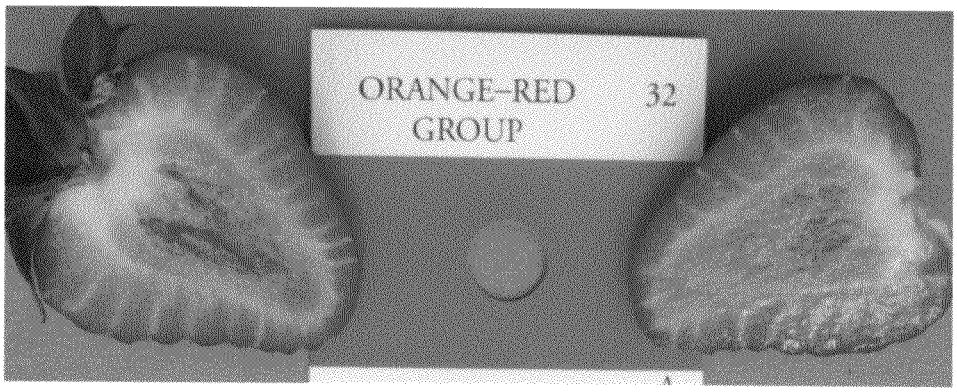

The photograph in FIG. 3 provides a close-up view of the berry flesh of 'SSL 93'.

Figure 4:
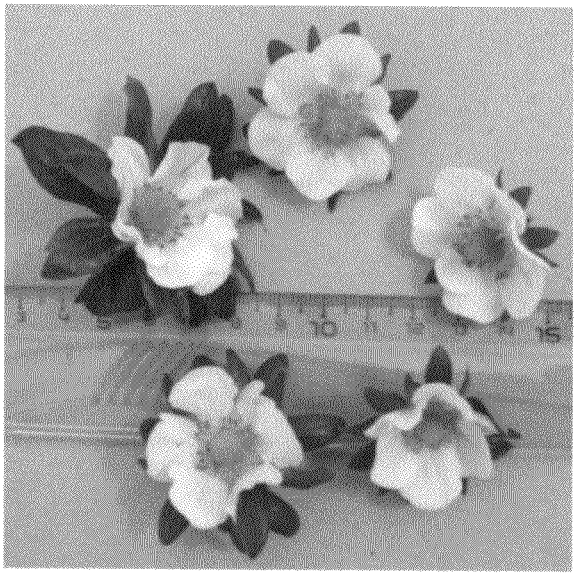

The photograph in FIG. 4 provides a close-up view of the flowers of 'SSL 93'.

The photographs depict color features as true as is reasonably possible with the digital photography methods used and the color values cited in the detailed botanical description accurately describe the new *Fragaria*.

DETAILED BOTANICAL DESCRIPTION

The following is a detailed description of five month-old plants of 'SSL 93' as grown in trial fields with tunnels and polyethylene covers in Cartaya, Huelva, Spain. The phenotype of the new cultivar may vary with variations in environmental, climatic, and cultural conditions, as it has not been tested under all possible environmental conditions. The color determination is in accordance with The 1995 R.H.S. Colour Chart of The Royal Horticultural Society, London, England, except where general color terms of ordinary dictionary significance are used.

General description:

*Blooming period*.—Mid-January through Mid-May in Cartaya, Huelva, Spain.

*Plant type*.—Herbaceous fruit producing perennial.

*Plant habit*.—Upright, semi-compact with dense canopy.

*Height and spread*.—Large; reaches an average of 33 cm in height and 34.5 cm in width.

*Cold Hardiness*.—Not tested in areas where temperatures of 32° F. occur.

*Diseases*.—Tolerance to *Botryotinia cinerea* and slight susceptibility to *Podosphaera leucotricha* (powdery mildew) and *Phytophtora cactorum* (crown rot).

*Root description*.—Fibrous, 10 days to initiate roots, 8 weeks to produce a rooted plant, NN155C in color.

*Propagation*.—Rooting of stolons.

*Growth rate*.—Vigorous.

*Stem description*.—Acaulescent.

*Stolon description*.—An average of 40, 27.45 cm in length and 0.61 mm in width, 144B and 145A in color, surface pubescence is medium.

Foliage description:

*Leaf division*.—Three leaflets.

*Leaf arrangement*.—Basal.

*Leaf attachment*.—Petiolate.

*Leaflet shape*.—Broadly ovate to rounded.

*Mid-tier leaflet size*.—Average of 8.1 cm in length and 9.04 cm in width.

*Leaflet margins*.—Serrate, slightly pointed to slightly rounded, an average of 19.5 serrations per leaf.

*Angle of terminal leaflet to petiole*.—30 degrees from vertical.

*Leaflet base*.—Asymmetrically oblique and rounded.

*Leaflet apex*.—Round.

*Leaflet glossiness*.—Upper surface medium, lower surface absent.

*Leaflet aspect*.—Some flat but most leaflets slightly concave.

*Leaflet interveinal blistering*.—Slight to moderate.

*Leaflet venation*.—Pinnate, coloration matched leaflet color.

*Leaflet surface*.—Upper surface glabrous, lower surface slight to moderate pubescent, particularly along the vein, with slight to moderate blistering depending on leaf age.

*Leaflet color*.—Upper surface 137A, lower surface 191A, no variegation present on either surface.

*Petiole*.—Round in shape, average of 30.54 cm in length and 5.2 mm in width, moderate to heavy pubescent surface (particularly heavy near base and close to stipules); hair attitude is horizontal, strong in strength, 144B and 145A in color.

*Petiolules*.—Round in shape, average of 8 mm in length and 4 mm in width, moderately pubescent surface, 145A in color.

*Stipule*.—Average of 3.52 cm in length and 1.18 cm in width, 55AB and C in color (weak to moderate anthocyanin), surface texture is slight to moderately pubescent.

Flower description:

*Inflorescence*.—Truss.

*Inflorescence size*.—Medium to long in length; average of 27.45 cm and 0.35 in width.

*Flower initiation and expression conditions*.—Temperature and day-length dependent.

*Time of flowering* (50% *of plants at first flower*).—Early to mid season.

*Number of flowers per truss*.—Average of 7.

*Flower position relative to foliage*.—Mostly even with some exposed above (about 10%).

*Flower size*.—Average of 3.48 cm in diameter and 2 cm in depth.

*Flower fragrance*.—Slight.

*Calyx*.—Position even, average of 4.96 cm in diameter, larger than corolla, flat to slightly re-curved relative to fruit.

*Sepals*.—Average of 12, oblong to oblanceolate, an average of 2.5 cm in length and 1.3 cm in width, 137A on upper surface, 191A on lower surface, truncate base, acuminate to acute apex, slightly pubescence surface on upper and lower surface.

*Sepal position*.—Mixed arrangement relative to the fruit, most re-curving, some horizontal with fruit shoulder, few touching the fruit shoulder.

*Petals*.—6 to 7, average of 1.4 cm in length and 1.6 cm in width, round in shape, obtuse base and apex, slightly overlapping, entire margins, upper and lower surface glabrous and 155C in color.

*Peduncle*.—145A in color, moderately pubescent surface, average of 5.33 cm in length and 0.61cm in width, strong in strength.

*Pedicel*.—145A in color, moderately pubescent surface; hair attitude is horizontal, strong in strength, average of 18.5 cm in length and 0.35 cm in diameter.

*Pistils*.—Average of 145, average of 1.1 mm in length, steeply dome shaped, 151B and 151C in color.

*Stigma*.—Club shaped and 154A and 154B in color.

*Style*.—Average of 1 mm in length and 154A to 154B in color.

*Stamens*.—Average of 26, average of 2.5 mm in length, shape is a cone-like tube and wider at the base, anther is oval in shape, average of 2 mm in length and 162B in color, pollen is moderate in quantity and 2A in color.

*Bracts*.—Observed on 80% of the flower trusses from early developmental stage, which progresses into a typical single leaflet as the truss matures and fruit develops with characteristics similar to leaflets.

Fruit description:

*Shape*.—Primarily conical to cordate with broad shoulders, shape is similar for primary, secondary and tertiary fruit.

*Season of harvest*.—End-January through Mid-May in Cartaya, Huelva, Spain.

*Time of ripening* (50% *of plants with first ripe fruit*).—Early.

*Type of bearing*.—Short day — Mediterranean.

*Size*.—Large to medium; an average of 5.28 cm in length and 4.3 cm in width.

*Surface*.—Smooth and highly glossy.

*Calyx position*.—Even to very slightly inserted and most re-curved.

*Attitude of calyx segments*.—Most re-curved, others touching the fruit shoulder, strong adherence to the fruit.

*Diameter of calyx relative to fruit diameter*.—Slightly larger, later in season size is similar to fruit diameter.

*Glossiness*.—Even and very high.

*External color* (*skin*).—Red group 44A and 44B, color is retained throughout the cropping season and holds up well to high seasonal temperatures.

*Internal color* (*flesh*).—Orange-red 32A.

*Evenness of color of skin*.—Very even.

*Evenness of color of flesh*.—Even.

*Acidity*.—Very low.

*Sweetness*.—Very high to high.

*Soluble solids*.—9.1

*Firmness*.—Skin is very firm (resistant to bruising), flesh is moderately firm.

*Juiciness*.—Moderate.

*Aroma*.—High.

*Weight*.—Average of 21 g per berry and 1,038 g per plant in a harvest season.

*Hollow center*.—Expressed on primary fruit, weakly or not present on secondary and tertiary fruit.

*Shelf life*.—An average of 8 to 10 days.

*Achene color.*—1B on shady side, 34B on sunny size.
*Achene position.*—Level with the surface.
*Achene number.*—An average of 250 per berry.
*Band within achenes.*—Very narrow.

It is claimed:

1. A new and distinct cultivar of strawberry plant named 'SSL 93' as herein illustrated and described.

* * * * *